US00PP08222P

United States Patent [19]

Ellison et al.

[11] Patent Number: Plant 8,222

[45] Date of Patent: May 4, 1993

[54] ASPARAGUS PLANT NAMED 'JERSEY JEWEL'

[75] Inventors: J. Howard Ellison, Milltown; John J. Kinelski, Princeton, both of N.J.

[73] Assignee: Rutgers University, New Brunswick, N.J.

[21] Appl. No.: 793,108

[22] Filed: Nov. 15, 1991

[51] Int. Cl.[5] ..... A01H 5/00

[52] U.S. Cl. ..... Plt./95

[58] Field of Search ..... Plt./95

*Primary Examiner*—James R. Feyrer

*Attorney, Agent, or Firm*—Frank B. Robb

[57] ABSTRACT

An $F_1$ male asparagus hybrid which is moderately resistant to asparagus rust (puccinia asparagi), tolerant to root and crown rot (*Fusarium oxysporum* f. sp. *asparagi*) as well as stem and crown rot (*F. moniliforme*), capable of producing high yields of high quality asparagus in many locations.

1 Drawing Sheet

BACKGROUND OF THE DISCLOSURE

The invention herein set forth is an asparagus plant which is one of the products of an extremely detailed long continuing program of asparagus development, since it is a valuable plant commercially and thus lends itself to expending effort and time in providing new and improved plants for commercial exploitation as well as desirable plants for home garden use.

As is well known, the primary method of producing asparagus ultimately is from seed which is the product of crossing male and female plants of selected characteristics.

We have also established, by causing the new plant to be asexually reproduced by crown division at Rutgers University, and, that the characteristics come true and are repeated from generation to generation.

The asparagus plant herein described in an $F_1$ asparagus hybrid resulting from the cross between the female plant 'Donna' U.S. Plant Pat. No. 5,652 and a male asparagus plant which we have named 'Austin' further denominated in our records as No. 50-2.

In the particular example of the plant herein described, it is designated in our records as No. 56×50-2, and in commercial use will be known as "Jersey Jewel".

DETAILED DESCRIPTION OF THE INVENTION

This particular plant is valuable primarily because it is a good commercial producer of high quality spears for use in commerce and particularly for the fresh market even though processors and home gardeners also can benefit from the supply of this particular plant.

As such the long continuing program which we have conducted has resulted in the selection of this particular plant for its ability to produce and it has indeed performed very well in certain locations where the climate is relatively dry and the growing season is long.

This is not true in all parts of the United States or other countries, but where those conditions prevail this plant is indeed a good and valuable addition to known asparagus varieties.

The hybrid hereof has been, as stated, initially produced from seed but it has also at our direction been caused to be asexually reproduced and established that the characteristics thereof have been found to continue from generation to generation and thus are fixed, in our judgment.

As will be understood from data supplied herewith, the data for production of the asparagus plant herein, is selected from test growing of the plants in South Africa, an unusual basis for comparison, but nevertheless illustrative of the value of this particular plant.

Figure 1:
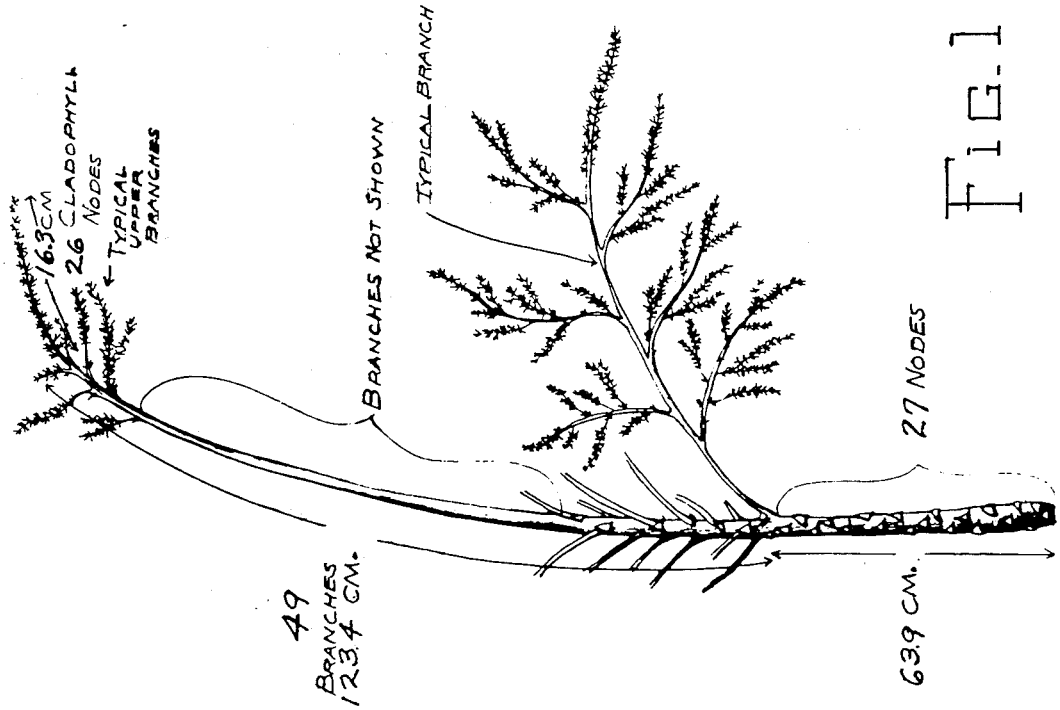

Turning to a consideration of the drawing which is attached hereto, as will be seen in FIG. 1, certain data of dimensions and positions of branches and other details are set forth and illustrating aspects of the plant by way of notation.

Figure 2:
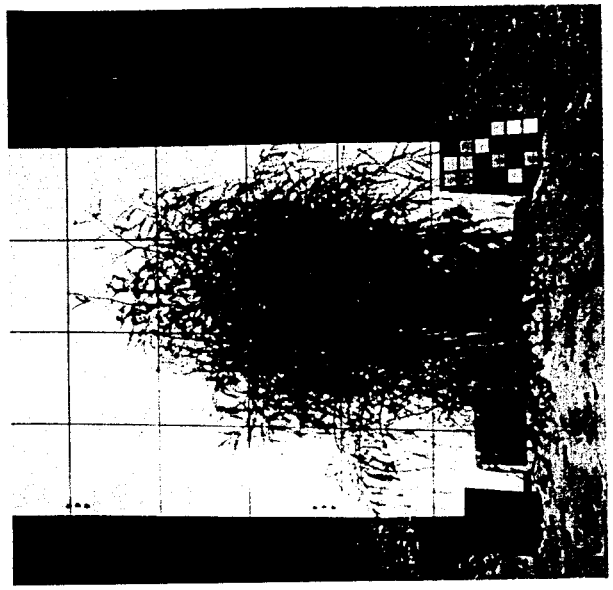

Additionally color data is supplied for the flowers and references made in that color data to the Munsell Color Limit Cascade and which color is illustrated in FIG. 2 of the drawing as being representative and the best way it can be shown in photographic reproduction processes currently available.

The values to follow are expressed in centimeters unless otherwise indicated. The number (1) indicates that the measurements presented were taken from the largest stalk.

*Stalk data:*

- *Number of nodes below first branch* (1).—27.
- *Number of cm from crown to first branch* (1).—63.9.
- *Number of branches* (1).—49.
- *Number cm between first and last branch* (1).—123.4.
- *Internode length in cm between branches* (1).—2.55.
- *Number of cladophyll nodes beyond last branch* (1).—26.
- *Number of cm beyond last branch* (1).—16.3.
- *Internode length in cm beyond last branch* (1).—0.63.
- *Largest stalk diameter in mm.*—14.0.
- *Mean diameter of three largest stalks in mm.*—13.2.
- *Number of stalks.*—9.
- *Stalk vigor index* (*No.* × *mean diameter*$^2$).—1,600.
- *Mature stalk color, bloom removed. Color No.*.*—21-12.
- *Crown to first branch of highest headed stalk cm.*—57.8.

Flower data:

- *Petal tip* (*yellow*) *Color No.*.*—24-9.
- *Petal base* (*green*) *Color No.*.*—24.12.
- *Flower length in mm.*—5.78.
- *Flower width at midpoint in mm.*—2.50.

Cladophyll data:

*Number per node.*—5.73.

*Length in mm.*—14.88.

*Width in mm.*—0.12.

TABLE 1

Yield of asparagus at Donald Cook Farms, Republic of South Africa.[z]

| Variety | 1981 | 1982 | 1983 | 1984 | 1985 | Total |
|---|---|---|---|---|---|---|
| Limbras | 328 | 823 | 908 | 1066 | 949 | 4074 |
| V15X50-9 | 524 | 818 | 906 | 1200 | 872 | 4320 |
| Jersey Jewel | 578 | 1715 | 1662 | 1810 | 1726 | 7491 |

[z]Planted in 1979

TABLE 2

Size and quality of asparagus spears - Donald Cook Farms, Republic of South Africa.[z]

| Variety | Spear weight grams/spear | Grade No. 1 % |
|---|---|---|
| Limbras | 10.1 | 14.0 |
| V15X50-9 | 12.6 | 47.9 |
| Jersey Jewel | 11.5 | 31.3 |

[z]Planted in 1979. Data from 1985 harvest.

We claim:

1. A new and distinct asparagus plant as shown and described herein, characterized particularly as to novelty by its ability to produce high quality asparagus spears for both commercial and fresh market use, also being suitable for good production of spears in home gardens, the hybrid being particularly well adapted to certain regions where climate is relatively dry and the growing season is long, the plant being moderately resistant to some of the known asparagus problems but producing unusually high yields of the quality aforesaid.

* * * * *